United States Patent [19]

Finger

[11] Patent Number: Plant 5,348

[45] Date of Patent: Nov. 20, 1984

[54] KALANCHOE PLANT NAMED BALI

[75] Inventor: Hermann Finger, Wiesmoor, Fed. Rep. of Germany

[73] Assignee: Wiesmoor-Gartnerei und Baumschule GmbH, Wiesmoor, Fed. Rep. of Germany

[21] Appl. No.: 477,894

[22] Filed: Mar. 23, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct Kalanchoe plant named Bali having vigorous growth habit and root system, highly floriferous habit, with orange colored flowers being formed at every shoot, freely branching, and by its suitability for production in 8 to 15 cm. pots.

1 Drawing Figure

The present invention relates to a new and distinctive cultivar of Kalanchoe plant, botanically known as Kalanchoe, and referred to by the cultivar name Bali.

The new cultivar was referred to during the breeding and selection process by the designation WG 2, and is a product of a planned breeding program. The basic objective of the breeding program was to create a new Kalanchoe cultivar having orange flowers, a vigorous root system, and good quality foliage and flowers.

The new cultivar was originated from a cross made in a controlled breeding program in Wiesmoor, West Germany. The female, or seed parent was a cultivar designated Regulus, disclosed in U.S. Plant Pat. No. 4,817. The male, or pollen parent was a cultivar designated Solferinopurpur, disclosed in U.S. Plant Pat. No. 3,843.

Bali was discovered and selected by me as a flowering plant within the progeny of the stated cross in a controlled environment in Wiesmoor, West Germany. Asexual reproduction of the new cultivar by stem cuttings, as performed by me at Wiesmoor, West Germany, has demonstrated that the combination of characteristics as herein disclosed for the new cultivar are firmly fixed and are retained through successive generations of asexual reproduction.

Bali has not been observed under all possible environmental conditions. The phenotype may vary significantly with variations in environment such as temperature, light intensity and day length. The following observations, measurements and values describe the new cultivar as grown in Wiesmoor, West Germany, under greenhouse conditions which closely approximate those generally used in commercial practice.

The following traits have been repeatedly observed and are determined to be basic characteristics of Bali, which in combination distinguish this Kalanchoe as a new and distinct cultivar:

(1) Bali was selected especially for its vigorous root system, which is much stronger than that of the maternal parent Regulus.

(2) Growth is more vigorous than that of either parent.

(3) Freely branching, comparable to that of Regulus.

(4) Proper scheduling makes Bali suitable for production in 8 to 15 cm. pots.

(5) To reduce peduncle elongation after flower initiation plants can be treated with Alar or B9.

(6) Bali is highly floriferous, with numerous orange flowers formed at every shoot.

(7) Flowering time is 11 weeks in summer to 14 weeks in winter after start of short days.

The new cultivar is most similar to its maternal parent Regulus. Bali is principally distinguished from Regulus by its much more vigorous root system and better growth.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under artificial light conditions approximately at noon in Wiesmoor, West Germany.

BOTANICAL CLASSIFICATION

Kalanchoe, cv. Bali.

PARENTAGE

Male parent: Solferinopurpur.

Female parent: Regulus. cl PROPAGATION

The new cultivar holds its distinguishing characteristics through successive propagations by leaf cuttings and by division of shoots.

Type cutting: Short tip cutting, with stems up to 2 cm. long.

Time to root: 10 days at 21° C. summer. 14 days at 21° C. winter.

Rooting habit: Many very fine roots, fibrous.

PLANT DESCRIPTION

Form: Short, compact, upright. Growing and scheduling practices can produce small plants in 8 cm. pots up to larger plants in 15 cm. pots.

Habit of growth: Rate of growth moderate for this type of plant. Generally, shoots are formed at every node.

Foliage description: Leaves simple, opposite, generally symmetrical, tending to be slightly folded upward from the main vein.

1. *Size.*—Average full grown leaves of flowering plants in 10 cm. pots are 100 mm. long and 70 mm. wide.

2. *Shape.*—Elliptic to ovate, apex acute to obtuse, base truncate.
3. *Texture.*—Glabrous, coriaceous, succulent.
4. *Margin.*—Dentate.
5. *Color.*—Young foliage top side, yellow green 147A, under side, yellow green 147B. Mature foliage top side yellow green 147A, under side, yellow green 147B.

FLOWERING DESCRIPTION

Flowering habit: Inflorescence of each shoot is formed by dichotomous branching, starting with opening of terminal flower of main axis, followed by terminal flowers of the side branches. Opening of new buds will continue for two months or more. Individual flowers last two weeks or more after opening.

Natural flowering season: January. Flowering time under controlled daylength at 20° C. in summer is 11 weeks; in winter at 20° C., 14 weeks. Flowering time depends on temperature, light intensity and other growing conditions.

Flower buds: Developing to tubular as flower petals mature, sheathed with four green sepals; corolla at maturity 9 mm. long.

1. *Size.*—Up to 11 mm. long.
2. *Shape.*—Generally oblong.
3. *Rate of opening.*—Opening of new buds will continue for two months or more.

Flowers borne: On compound dichasial cymes on strong peduncles. Peduncle length depends on growing conditions and applications of Alar or B9; pedicels up to 5 mm. long.

Quantity of flowers: Highly floriferous. Main axis and side shoots have 100 or more flowers.

Petals:

1. *Shape.*—Elliptic to nearly round, apex cuspidate.
2. *Color.*—Top side when opening, orange red 33A, fading to orange red 30B; under side orange red 33C.
3. *Number and size of petals.*—Four, united in corolla, salverform; petals 6 mm. in diameter, total flower diameter 15 mm.

Reproductive Organs:

1. *Stamens.*—Eight (8) in number. (a) Anther shape: flat, elliptical, color light brown. (b) Filament color: light green. (c) Pollen color: yellow.
2. *Pistels.*—(a) Stigma shape: flat, crystalline, color greenish white. (b) Style color: light green. (c) Ovaries: 4 celled, 6 mm. long, color yellow green 144C.

DISEASE RESISTANCE

No known Kalanchoe diseases observed to date.

I claim:

1. A new and distinct Kalanchoe plant named Bali, as described and illustrated, and particularly charcterized by its vigorous growth habit and root system, highly floriferous habit, with orange colored flowers being formed at every shoot, freely branching, and by its suitability for production in 8 to 15 cm. pots.

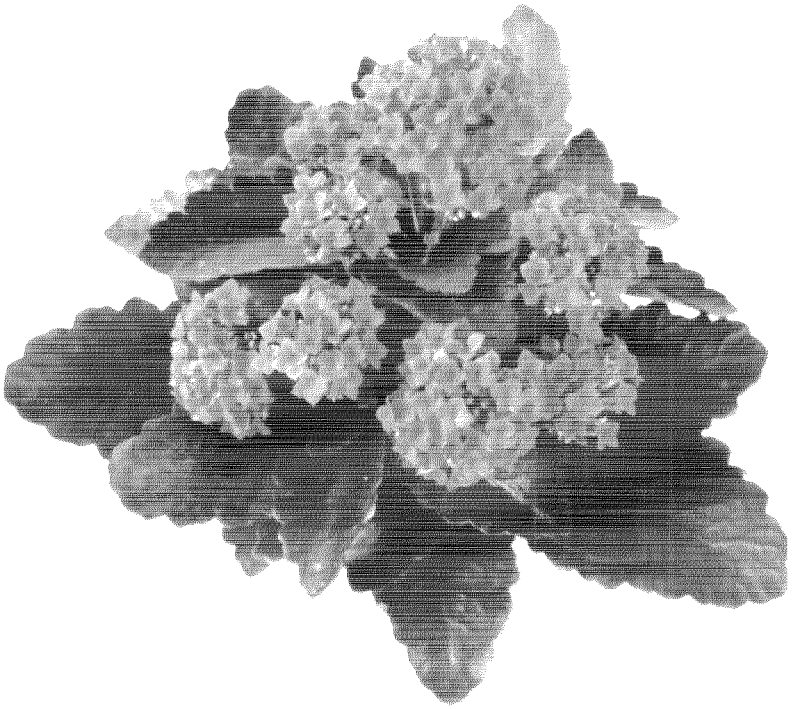

* * * * *